United States Patent
Zakharov et al.

(10) Patent No.: US 9,823,138 B2
(45) Date of Patent: Nov. 21, 2017

(54) NON-INVASIVE AUTOMATIC MONITORING OF PET ANIMAL'S CORE TEMPERATURE

(71) Applicant: PetPace LTD, Ramat Hasharon (IL)

(72) Inventors: Michael Zakharov, Tel Aviv (IL); Asaf Dagan, Herzliya (IL); Michael Bukchin, Haifa (IL); Abraham Menkes, Ramat Hasharon (IL)

(73) Assignee: PETPACE LTD, Ramat Hasharon (IL)

( * ) Notice: Subject to any disclaimer, the term of this patent is extended or adjusted under 35 U.S.C. 154(b) by 703 days.

(21) Appl. No.: 13/971,902

(22) Filed: Aug. 21, 2013

(65) Prior Publication Data

US 2015/0057963 A1 Feb. 26, 2015

(51) Int. Cl.
*G01K 13/00* (2006.01)
*A61B 5/01* (2006.01)
(Continued)

(52) U.S. Cl.
CPC .......... *G01K 13/002* (2013.01); *A01K 29/005* (2013.01); *A61B 5/01* (2013.01);
(Continued)

(58) Field of Classification Search
CPC ........... A01K 29/005; A61B 5/01; A61B 5/11; A61B 2503/40; A61B 2560/0252; G01K 13/002; G01K 7/427
(Continued)

(56) References Cited

U.S. PATENT DOCUMENTS 3,781,837 A * 12/1973 Anderson ................ A61B 5/01
340/573.1
4,436,092 A * 3/1984 Cook ................... A61N 1/3655
607/21
(Continued)

FOREIGN PATENT DOCUMENTS

WO 0207644 1/2002
WO 03087737 10/2003

OTHER PUBLICATIONS

Andrea, A Canine Temperature, Three-Little-Pitties, Dec. 2011, pp. 1-2.*

*Primary Examiner* — Alexander Satanovsky
*Assistant Examiner* — Lina Cordero
(74) *Attorney, Agent, or Firm* — Mark M. Friedman

(57) ABSTRACT

A system, device and method monitoring whether a core temperature of a warm-blooded pet animal is within a normal range for the pet animal comprises a sensing assembly including (i) a skin temperature sensor positioned such that a sensing surface of the skin temperature sensor faces the animal, the skin temperature sensor configured to produce a skin temperature output, (ii) an ambient temperature sensor spaced away from the animal and configured to produce an ambient temperature output, and (iii) an accelerometer for sensing an acceleration of the pet animal and producing an acceleration output; and a processor for receiving the outputs, calculating an activity level from the acceleration data and determining whether the core temperature (Continued)

of the pet animal is within the normal range based on a pre-defined function relating the skin temperature $T_S$, the ambient temperature $T_A$, and the activity level of the pet animal.

17 Claims, 8 Drawing Sheets

(51) Int. Cl.
  *A61B 5/11* (2006.01)
  *A01K 29/00* (2006.01)
  *G01K 7/42* (2006.01)
(52) U.S. Cl.
  CPC ............... *A61B 5/11* (2013.01); *A61B 5/1118* (2013.01); *G01K 7/427* (2013.01); *A61B 2503/40* (2013.01); *A61B 2560/0252* (2013.01)
(58) Field of Classification Search
  USPC ........................................................ 119/859
  See application file for complete search history.

(56) References Cited

U.S. PATENT DOCUMENTS

| | | | | |
|---|---|---|---|---|
| 5,724,025 A | * | 3/1998 | Tavori | A61B 5/0002 340/573.1 |
| 6,487,992 B1 | * | 12/2002 | Hollis | A01K 15/021 119/712 |
| 2005/0234349 A1 | | 10/2005 | Pravica | |
| 2006/0155172 A1 | * | 7/2006 | Rugg | A61B 5/1113 600/300 |
| 2008/0021352 A1 | * | 1/2008 | Keegan | A61B 5/0002 600/595 |
| 2008/0058670 A1 | * | 3/2008 | Mainini | A61B 5/0002 600/549 |
| 2008/0110414 A1 | * | 5/2008 | Buehner | A01K 13/006 119/712 |
| 2008/0170600 A1 | * | 7/2008 | Sattler | G01K 1/16 374/163 |
| 2009/0149727 A1 | * | 6/2009 | Truitt | A61B 5/14552 600/323 |
| 2012/0068848 A1 | * | 3/2012 | Campbell | A61B 5/0008 340/573.1 |
| 2013/0014706 A1 | * | 1/2013 | Menkes | A61D 13/00 119/859 |
| 2013/0030242 A1 | * | 1/2013 | Ruehring | A61B 9/00 600/28 |
| 2014/0083364 A1 | * | 3/2014 | Anderson | A01K 5/01 119/51.01 |
| 2014/0128753 A1 | * | 5/2014 | Luna | A61B 5/02438 600/500 |
| 2014/0275824 A1 | * | 9/2014 | Couse | A01K 29/005 600/301 |

\* cited by examiner

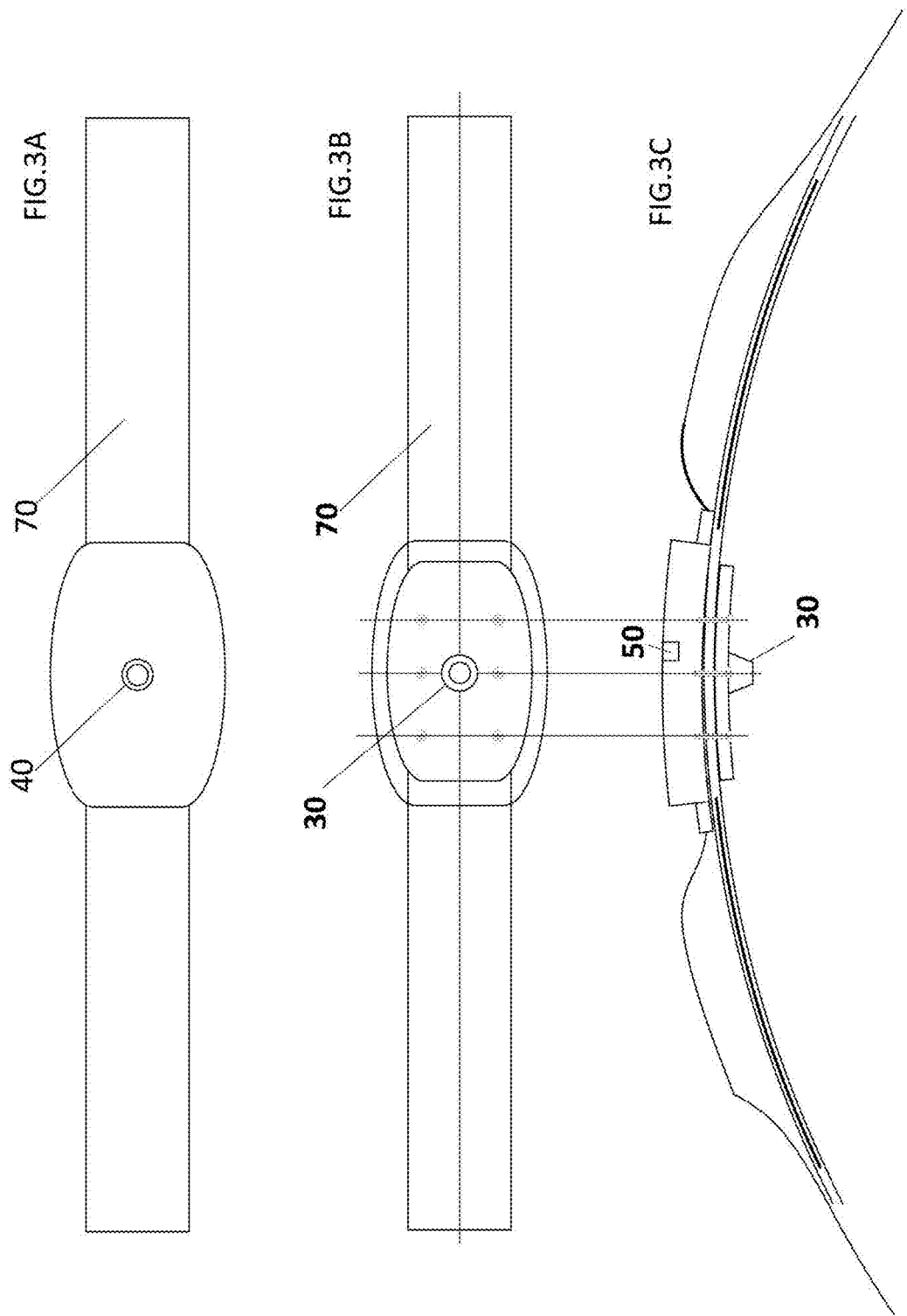

NON-INVASIVE AUTOMATIC MONITORING OF PET ANIMAL'S CORE TEMPERATURE

FIELD AND BACKGROUND OF THE INVENTION

The present invention relates to apparatuses and methods for monitoring health of animals, and, more particularly for monitoring the health through estimation of thermoregulation ability based on a combination of the animal's skin temperature, ambient temperature and activity level.

When animals, including pets such as dogs and cats, are sick they tend by their natural survival instinct to hide their symptoms and weakness. This behavior makes detection by the caretaker of the disease or condition of the pet significantly more difficult. Usually, by the time a pet reaches the veterinarian its medical condition is already advanced.

Veterinarians commonly apply standard medical protocols to assess the health condition of a patient. Measuring vital signs, including rectal temperature, is an essential part of such protocols. Rectal temperature serves as an indication of the patient's core body temperature and thermoregulatory ability and as such helps to detect development of disease conditions, evaluate their severity and monitor response to treatment.

Early detection of core body temperature changes is important in animals since it allows timely, and sometimes life-saving, interventions in acute situations such as heat stroke, hypothermia, and acute infections. Moreover, certain populations of pets benefit significantly from more frequent temperature measurements and their medical treatment dramatically improves. Examples of such populations include dogs and cats undergoing chemotherapy, hospitalized pets at risk of contracting an infection and those receiving immune-suppressive medications. Early and accurate detection of changes in core body temperature in these pets have been shown to correlate with improved survival and longevity.

In veterinary medicine, estimation of core body temperature and thermoregulation capacity is routinely done by a slightly invasive method, using standard over-the-counter human thermometers, inserted into the animal's rectum for several seconds. It is well known that rectal temperature does not always accurately imply core body temperature, but for practical reasons, and lack of suitable alternatives, it is the accepted clinical standard. However, measurement of rectal temperature is uncomfortable for the animal and occasionally difficult to perform if the pet animal is not cooperative, which is especially true for cats. Moreover, in some clinical situations rectal measurement becomes impossible, for example if some disease, wound or surgery is affecting the rectal area and preventing access. For practicality reasons, it is only rarely done by owners in a home setting. The result of these practical limitations is that temperature measurements on pets are performed less frequently than desired or required, even in the hands of professionals in a vet clinic or hospital, leading to a lower level of medical monitoring and care for pets.

Alternative, non-invasive techniques to measure temperature, like infra-red ear or skin thermometers, were found in clinical studies to be inaccurate, inconsistent, and unreliable. On the other hand, there is some use of invasive temperature sensors that are swallowed by the animal and transmit data while passing down the animal's intestines. The use of these devices is limited to research facilities. The cumbersome and sometimes difficult rectal method is therefore the one used clinically today.

Several attempts have been made to construct systems for remote monitoring of the animal's temperature. Such prior art systems typically require ingestible or implantable devices which make these systems unsatisfactory for the task of monitoring the pet animal. For example, battery life of ingestible devices can hardly be of appropriate duration because of strong dimension limitations defined by typical size of the pet animal.

There is a compelling need to have an apparatus and method that will provide early detection of temperature changes of pet animals such as dogs and cats, and to do so accurately and efficiently without interfering with the comfort and normal behavior of the animal. It would be particularly helpful if there was a way to measure core temperature continuously, remotely, non-invasively, accurately and reliably.

SUMMARY OF THE PRESENT INVENTION

One aspect of the present invention is a system for monitoring whether a core temperature of a warm-blooded pet animal is within a normal range for the pet animal, the system comprising a sensing assembly including (i) a skin temperature sensor positioned such that a sensing surface of the skin temperature sensor faces a body of the pet animal, the skin temperature sensor configured to produce a skin temperature output, (ii) an ambient temperature sensor spaced away from the body of the animal and configured to produce an ambient temperature output, and (iii) an accelerometer for sensing an acceleration level of the pet animal and producing an acceleration output; and a processor for receiving the skin temperature output, the ambient temperature output and the acceleration level output and for determining whether the core temperature of the pet animal is within the normal range based on a pre-defined function relating the skin temperature output, $T_S$, the ambient temperature output, $T_A$, and an activity level, A, of the pet animal, the activity level, A, determined by the processor from the acceleration output.

A further aspect of the present invention is a method of monitoring a core temperature of a pet animal, the method comprising a temperature sensor of a sensor assembly facing a body of the pet animal and sensing and outputting a skin temperature of the pet animal; an ambient temperature sensor on an outer surface of the sensor assembly sensing and outputting an ambient temperature; an accelerometer of the sensor assembly sensing and outputting an acceleration of the pet animal; transmitting the outputs of the skin temperature, ambient temperature and acceleration to a processor configured to calculate an activity level of the pet animal from the acceleration, the processor determining whether the pet animal's core temperature is in a normal range based on a pre-defined function relating the skin temperature, the ambient temperature and the activity level.

A still further aspect of the present invention is a method of determining if an animal's core temperature is within a normal range, comprising sensing, and obtaining data for, a measured ambient temperature $T_A$, skin temperature $T_S$, and acceleration data; calculating activity level A from the acceleration data; using Ta to select a zone from (i) a thermoneutral zone, (ii) a zone below lower critical temperature (Tlc) and (iii) a zone above upper critical temperature (Tuc); obtaining one or more coefficients; calculating a baseline of a model; using activity A and coefficients to calculate a tolerance range; and determining whether the animal has a normal core temperature based on whether the skin temperature at ambient temperatures within the selected zone is within the tolerance range.

A yet still further aspect of the present invention is a device for monitoring whether a core temperature of a warm-blooded pet animal is within a normal range for the pet animal, the device comprising a sensing assembly including (i) a skin temperature sensor positioned such that a sensing surface of the skin temperature sensor faces a body of the pet animal, the skin temperature sensor configured to produce a skin temperature output, (ii) an ambient temperature sensor spaced away from the body of the animal and configured to produce an ambient temperature output, and (iii) an acceleration sensor for sensing an acceleration of the pet animal and producing an acceleration output; and a processor for receiving the skin temperature output, the ambient temperature output and the acceleration output, calculating an activity level from the acceleration output and for determining whether the core temperature of the pet animal is within the normal range based on a pre-defined function relating the skin temperature $T_S$ output, the ambient temperature $T_A$ output and the activity level of the pet animal.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 3A is a top view of a device or system including a mounting device in the form of a collar, in accordance with one embodiment of the present invention;

FIG. 3B is a bottom view of a device or system including a mounting device in the form of a collar, in accordance with one embodiment of the present invention;

FIG. 3C is a side view of a device or system including a mounting device in the form of a collar, in accordance with one embodiment of the present invention;

DETAILED DESCRIPTION OF THE INVENTION

Figure 1:
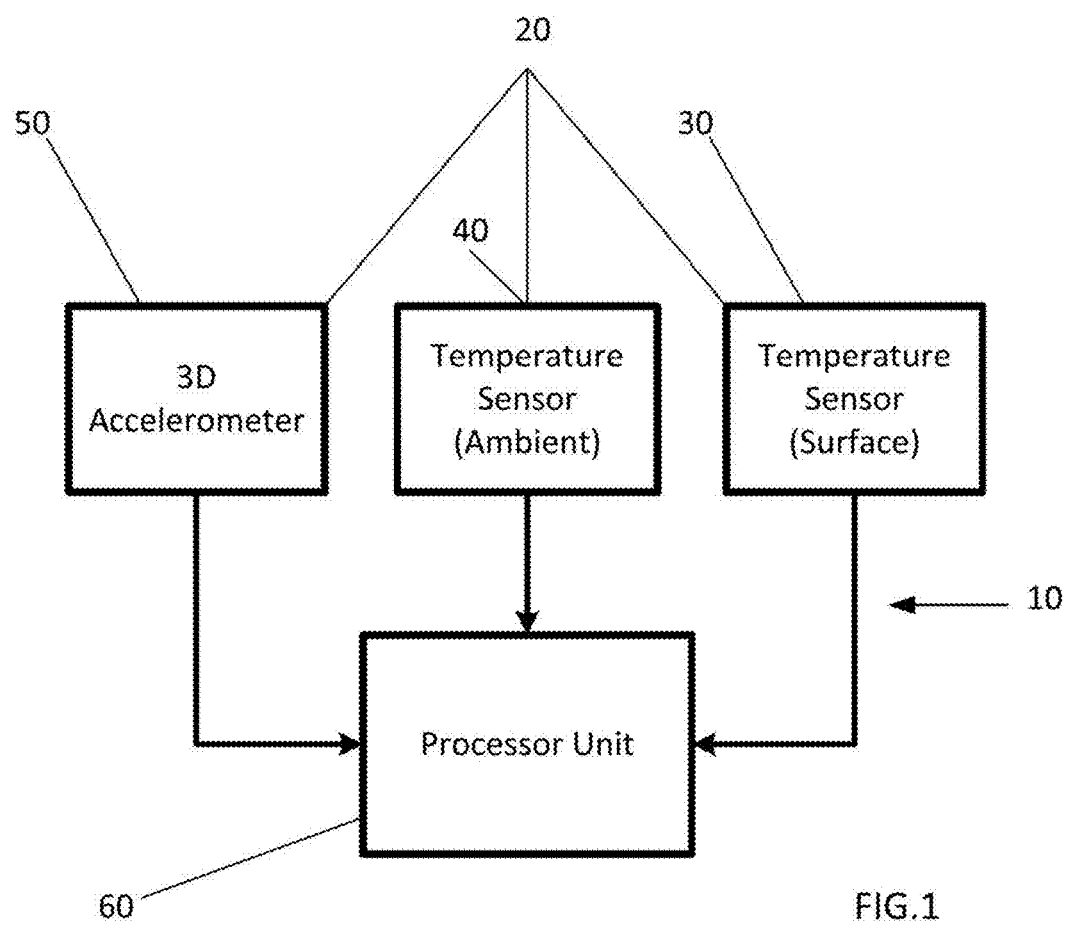
FIG. 1 is a block diagram of a device or system, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a device, system and method for monitoring the health of pet animals such as dogs and cats and other warm-blooded animals other than birds, such as by determining if the core temperature of the pet animal is inside a proper (normal) range of temperatures. Mammals, including dogs and cats, maintain homeostasis, which involves, among other things, keeping internal, or core body temperature, constant or within a relatively narrow normal range.

The device and system may include (i) a sensor assembly that may include a skin temperature sensor positioned such that a sensing surface of the skin temperature sensor faces a body of the pet animal, the skin temperature sensor configured to produce a skin temperature output, (ii) an ambient temperature sensor spaced away from the body of the animal and configured to produce an ambient temperature output, and (iii) an accelerometer for sensing an acceleration of the pet animal and producing an activity level output. The device and/or a system of the present invention may also include a processor for receiving the skin temperature output, the ambient temperature output and the acceleration output and for determining whether the core temperature of the pet animal is within the normal range, for example based on a pre-defined function relating the skin temperature $T_S$ the ambient temperature $T_A$, and the activity level of the pet animal, the processor determining the activity level from the acceleration data. The device and system may non-invasively monitor whether the pet animal's core temperature is within a normal range, the processor determining whether the core temperature is in the normal range based on whether the skin temperature output is within a confidence interval, the confidence interval defined by the kind and/or a size of the pet animal and based on the ambient temperature output, the skin temperature output and the acceleration output. Conversely, a non-normal determination by the processor may result in a report or signal that the animal is not within normal temperature conditions and may need treatment.

Because the core temperature of a healthy warm-blooded animal is usually constant, e.g. 38 degrees Celsius for dogs, with a tolerance of about 1.5 degrees Celsius, it means that some thermoregulation mechanisms are involved and the animals permanently expel the heat produced by their metabolism which leads to a correlation between the skin surface temperature of the animal and the ambient temperature around the animal. If the skin temperature is not within an appropriate range, the animal may be in an unhealthy condition and investigation may be required. The normal healthy range for the skin temperature may also depend on the activity level of the animal (relative to its current agility and fitness level) because any high level of activity may involve correspondingly high levels of muscular work, which in turn may generate increased metabolism and increased rate of generation of heat. Activity level may for example be calculated, for example by processor 60, from the acceleration data in accordance with the Vector Dynamic Body Acceleration methodology, which can be found in the scientific literature.

A preferred embodiment of the present invention utilizes a pet animal's thermoregulation mechanics to indicate whether the core temperature is maintained within an appropriate range. It uses the temperature difference between skin of the animal and its environment as an estimate of the heat loss by the animal and activity level as an estimate of the animal's metabolism rate. These values are then correlated to determine if the core temperature may not be in the proper (normal) range. Changes in core body temperature may indicate a pathologic process (e.g. viral infection) or an overwhelming effect of external factors on the animal (e.g. heat stroke). The present invention makes use of these facts.

In contrast to prior art pet animal collars and other devices or methods, which may not specifically measure core temperature of the pet animal, the device, system and method of the present invention may measure core temperature of the pet animal. In further contrast to prior art pet animal devices, which may be invasive, the device, system and method of the present invention may monitor the pet and determine its conditions automatically while still doing so non-invasively. In still further contrast to prior art devices and methods for animal, which may measure specific parameters, such as temperature, but which may not determine whether the pet animal is in a normal condition, the device, system and method of the present invention may in preferred embodiments provide a determination automatically and in an ongoing manner as to whether the core temperature of the animal is normal. In still further contrast to prior art monitoring devices and methods, which may not relate a particular parameter to a second or further parameter in a meaningful way, for example in a way that allows one to deduce important health conclusions, the present invention may utilize a formula to relate three parameters of the pet animal, one to the other. For example, a formula of the present invention, in one preferred embodiment, may relate the skin temperature of the pet animal, the ambient temperature for example adjacent or near the animal and the activity level of the animal together to yield a conclusion that the core temperature of the animal is within a normal range for healthy pet animals. In further contrast to certain prior art monitoring device and systems and methods, which only recommend analyze certain data from sensing elements but do not spell out the analysis, and therefore cannot be implemented to actually automatically monitor and determine the core temperature of the pet animal, the device, method and system of the present invention in certain preferred embodiments may utilize a specific formula wherein a processor of the present invention may determine whether the core temperature of the animal is normal by a pre-defined function relating the skin temperature $T_S$, the ambient temperature $T_A$, and the activity level of the pet animal. The pre-defined function may include an equation $T_S=a*T_A+b$ that is operative within a range of $T_A$, wherein $T_S$ is a variable of the skin temperature, $T_A$ is a variable of the ambient temperature and a and b are coefficients that are set depending upon the range of $T_A$ as well as on an animal size and kind. The range may be one of (i) a range below a lower critical temperature (Tlc), (ii) a range above an upper critical temperature (Tuc) and (iii) a thermoneutral range between the lower critical temperature (Tlc) and the upper critical temperature (Tuc). The pre-defined function may also include equations defining an upper margin of the skin temperature to be equal to $c_1*A+d_1$, and defining a lower margin of the skin temperature to be equal to $c_2*A+d_2$, wherein A is the activity level and wherein coefficients $c_i$ and $d_i$ are set depending upon on activity units and depending on animal kind and/or size. In further contrast to certain prior art monitoring device and systems and methods, the device, method and system of the present invention may in certain preferred embodiments be founded on empirical evidence, that automatically determines the core temperature of the pet animal from three parameters that are sensed by the three sensors. In still further contrast to the prior art, in which the determination may not be specific to a pet animals of a specific kind and size, in the present invention, the determination of the pet animal's health may be specifically tailored to pet animals of specific sizes and kinds. This may be accomplished because, for example, the coefficients in the formula used in the method, device and system of the present invention may be selected based on experience accumulated from experiments on pet animals of various kinds and sizes. The results of these experiments may set coefficients in equations relating the skin temperature to the ambient temperature within a confidence interval determined by the activity level.

The principles and operation of a method and apparatus for a pet animal core temperature monitor may be better understood with reference to the drawings and the accompanying description.

Reference herein to the "kind" of pet animal is a reference to the species of the pet animal, for example whether the particular pet animal is a dog, a cat or another species. The "kind" of pet animal may also include the breed, age and gender of the pet animal, if different breeds, ages and genders have different core temperatures and/or different coefficients for the predefined functions referred to herein.

As seen from FIGS. 1-6, the present invention may be described as a system 10 for monitoring the core temperature of a pet animal. The present invention may be described as a system 10 (or in some preferred embodiments a device 10) for monitoring whether core temperature of a warm-blooded pet animal is within a normal range for that pet animal.

System 10 of the present invention may include the sensor assembly 20 comprised of at least two temperature sensors, one for the animal's body surface temperature measurement (called a surface temperature sensor or sometimes called skin temperature sensor), and another for the environment temperature measurement, for example the ambient temperature. The sensor assembly 20 may also include at least one three-dimensional accelerometer for measuring the acceleration of the pet animal.

System 10 may include a sensor assembly 20 that may include (i) at least one skin temperature sensor 30 positioned such that a sensing surface of the skin temperature sensor faces a body of the pet animal 14 (FIG. 2), the skin temperature sensor configured to produce a skin temperature output, (ii) at least one ambient temperature sensor 40 spaced away from the body of the animal and configured to produce an ambient temperature output, and (iii) an accelerometer 50 for sensing an acceleration of the pet animal and for producing an acceleration output from which a processor of the system 10 may be configured to calculate an activity level of the pet animal using, for example, a separate algorithm. The sensor assembly 20 may be situated within a housing 90, for example an electronics case 90 (see FIG. 2).

The sensor assembly 20 may have an inner surface 22 that may be configured to conform generally or specifically to a neck or other body part of the pet animal. Skin temperature sensor 30 on the inner surface 22 may be configured to abut the body of the animal and produce a skin temperature output. Design of the inner surface 22 should be comfortable for mounting on the pet animal avoiding frictions, pressure, annoying etc. to the body of the pet animal.

Ambient temperature sensor 40 may be positioned on the outer surface 24 of sensor assembly 20 and may be situated at a minimum distance from the inner surface 22 of the sensor assembly 20 to ensure that ambient temperature sensor is distanced from the body of the pet animal. In a preferred embodiment, the ambient temperature sensor 40 may be distanced from the body by the distance in the range of 1-3 cm in order to prevent heating of the sensor from the body.

In addition, outer surface 24 of sensor assembly 20 may be configured such that between inner surface 22 and outer surface 24 or within one side of outer surface 30 there are materials of sufficient non-heat conducting nature so the skin temperature of the animals does not transfer heat to the ambient temperature sensor.

Sensor assembly 20 may also have an accelerometer 50 for sensing acceleration and producing an acceleration output of the pet animal. The processor may calculate an activity level from this acceleration output.

The whole sensor assembly, and the processor, may be positioned non-invasively relative to the pet animal. Accordingly, no invasive measurements need be taken for the method, device and system of the present invention to monitor and/or determine whether the core temperature of the animal is within the normal range.

Figure 2:
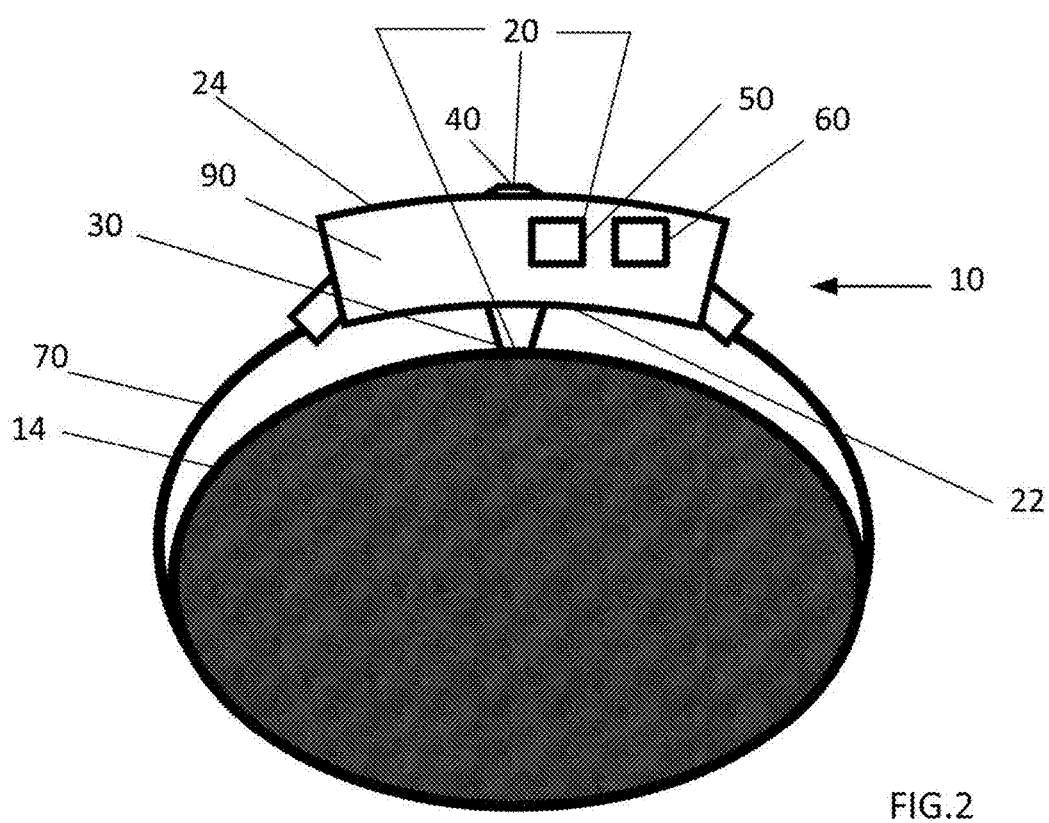
FIG. 2 is schematic view of a device or system, in accordance with one embodiment of the present invention.
Figure 5:
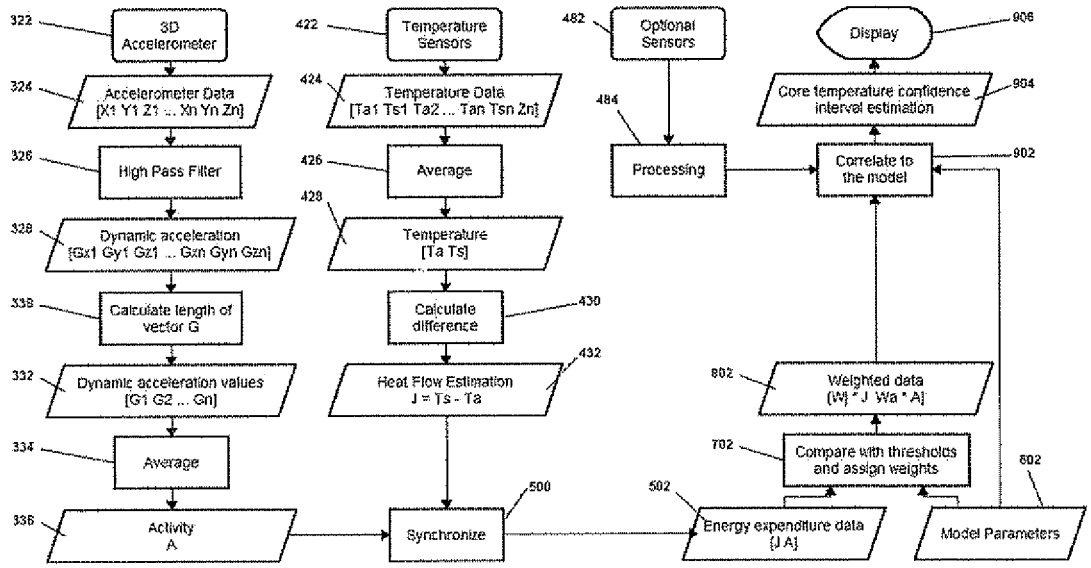
FIG. 5 is a flow chart of a system, device and/or method, in accordance with one embodiment of the present invention.

As seen from the block diagram of FIG. 1, from FIG. 2, and from the flow chart of FIG. 5, system 10 may also include a processor 60 for receiving the skin temperature output, the ambient temperature output and the acceleration output and for determining whether the core temperature of the pet animal is within a normal range. For example, in a preferred embodiment, the processor is configured to calculate a confidence interval (also called a "tolerance range") for the skin temperature output based on the skin temperature output, ambient temperature output and activity level, the activity level calculated from the acceleration data. The core temperature of the pet animal is defined to be in the normal range for that animal when the skin temperature output is within the confidence interval. The processor may also take into consideration specific characteristics of the animal such as kind (breed, age, gender, etc.) and size.

Processor 60 may be configured to analyze the outputs and compute whether the core temperature is within a normal range based on the pre-defined function relating the skin temperature output, the ambient temperature output and the activity level (which is calculated from the acceleration output data).

Processor 60 may determine whether the core temperature is in the normal range based on whether the skin temperature output is within a confidence interval. The processor 60 may determine the confidence interval based on the ambient temperature output, the skin temperature output and the acceleration output. In a preferred embodiment, the processor 60 bases the confidence interval ("tolerance range") also on physical properties of the animal such as the size of the animal and the kind of animal.

The confidence interval may be defined to be between an upper margin of the skin temperature, upper margin defined to be equal to $c_1*A+d_1$, and a lower margin of the skin temperature, the lower margin defined to be equal to $c_2*A+d_2$, wherein A is the activity level and wherein coefficients $c_i$ and $d_i$ are set depending upon on activity units and animal kind or size.

Figure 6:
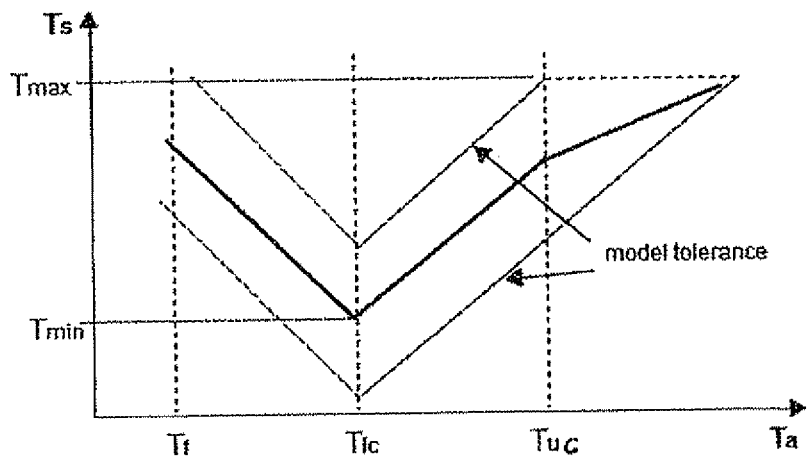
FIG. 6 is a graphical representation of the model showing a relationship between skin temperature of a pet animal and ambient temperature surrounding the animal, in accordance with one embodiment of the present invention.

The pre-defined function may include an equation $T_S=a*T_A+b$ that is operative within a zone of $T_A$, wherein $T_S$ is a variable of the skin temperature, $T_A$ is a variable of the ambient temperature and a and b are coefficients that are set depending upon an animal size and kind. In the preferred embodiment, the ambient temperature output is an independent variable and the skin temperature output is a dependent variable dependent on the ambient temperature. In certain preferred embodiments, the ambient temperature output is split up into segments, as shown in FIG. 6. The segments may be described as zones, such as temperature zones. A zone may be one of (i) a zone below a lower critical temperature (Tlc), (ii) a zone above an upper critical temperature (Tuc) and (iii) a thermoneutral zone between the lower critical temperature (Tlc) and the upper critical temperature (Tuc).

As seen from FIG. 2, processor 60 may form part of a device that may be mounted on the pet animal or processor 60 may be situated remotely with respect to the pet animal. Either way, processor 60 may be connected to sensor assembly 20 by a wired or a wireless connection. If processor 60 is remote, the sensor assembly 20 may be accompanied by a transmitter that transmits the outputs of the sensor assembly 20 to the remote processor. If processor 60 is on the animal, the determination reached by processor 60 may still be transmitted remotely. Alternatively, processor 60 may be in communication with a remote computer that may recalculate a determination arrived at by the processor 60 for further processing, for example as to whether the pet animal has a normal core temperature.

In the event that processor 60 is located on the animal as part of a single device together with the sensor assembly 20, what has been described as system 10 may also be characterized as a device 10. For example, a device 10 for monitoring whether a core temperature of a warm-blooded pet animal is within a normal range for the pet animal may comprise a sensing assembly 20 including (i) at least one skin temperature sensor 30 positioned such that a sensing surface of the skin temperature sensor faces a body of the pet animal, the skin temperature sensor configured to produce a skin temperature output, (ii) at least one ambient temperature sensor 40 that may be spaced away from the body of the animal and configured to produce an ambient temperature output, and (iii) an activity level sensor 50, such as an accelerometer, for sensing an acceleration of the pet animal. Device 10 may also include a processor 60 for receiving the skin temperature output, the ambient temperature output and the acceleration output, for calculating an activity level from the acceleration output and for determining whether the core temperature of the pet animal is within the normal range based on a pre-defined function relating the skin temperature $T_S$ output, the ambient temperature $T_A$ output and the activity level of the pet animal. The processor may be configured to determine whether the surface temperature is within a confidence interval, the confidence interval defined to be between an upper margin of the skin temperature, the upper margin defined to be equal to $c_1*A+d_1$, and a lower margin of the skin temperature, the lower margin defined to be equal to $c_2*A+d_2$, wherein A is the activity level and wherein coefficients $c_i$ and $d_i$ are set depending upon on activity units and animal kind or size.

Figure 2A:
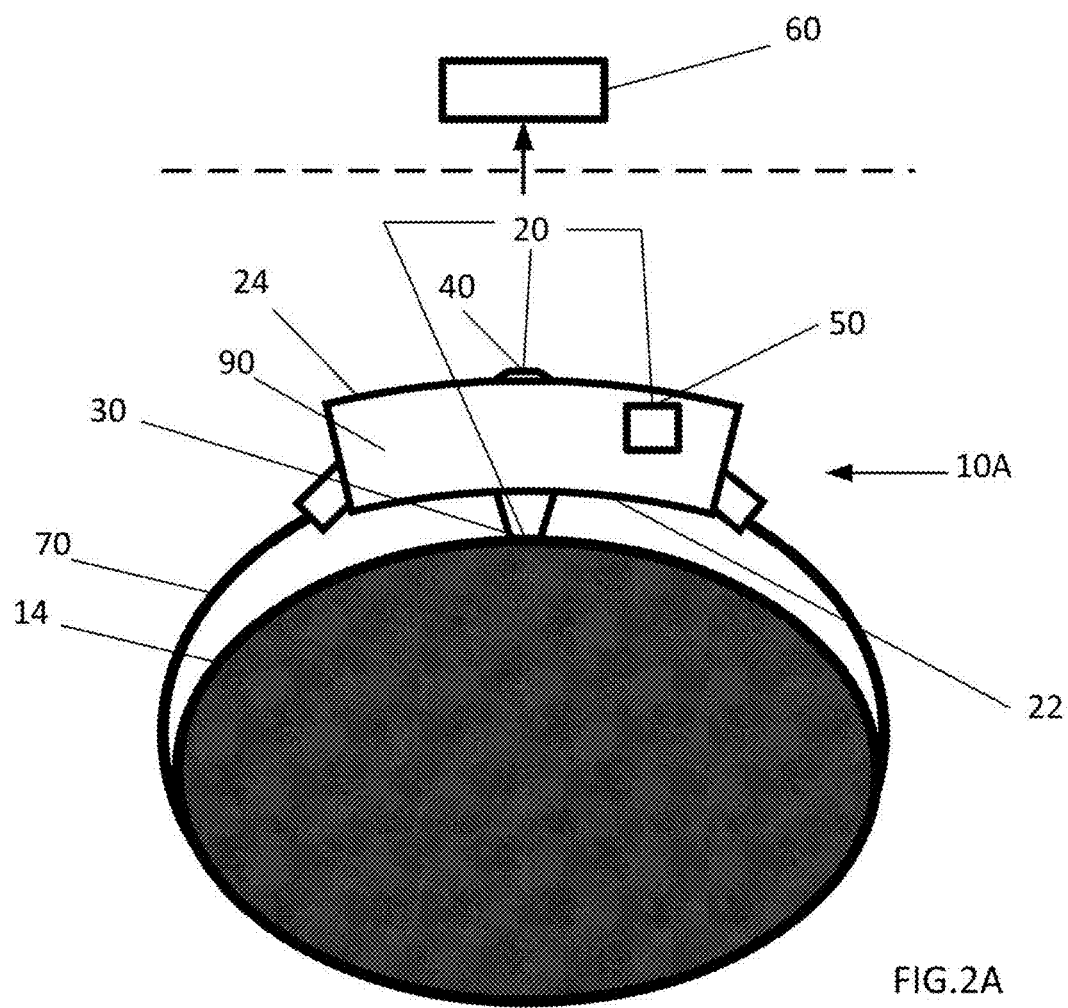
FIG. 2A is schematic view of a system in which processor 60 is remote from the sensor assembly 20, in accordance with one embodiment of the present invention.

Processor 60 may be the same for a device 10 as for a system 10, although anything necessary for sensor assembly 20 to transmit its outputs to a remote processor 60, as opposed to a local processor 60 may distinguish system 10 in which processor 60 is remote from device 10. It is noted that if processor 60 is remote from the animal and not part of a single device together with sensor assembly 20, the present invention would not ordinarily be considered a device but would have to be considered a system 10A, as shown in FIG. 2A.

The present invention may also be described as a device 10 that comprises sensor assembly 20 together with a mounting element 70 without a processor (although not device 10, which is defined to include a processor 60). Such a device may also include a transmitter for transmitting the outputs of the sensors to a processor, for example a remote processor.

Device 10 (wherein processor 60 is part of a single device 10 positioned on the pet animal being monitored) or system 10 or system 10A, may also include a transmitter for transmitting the determination or output of the processor 60 to a remote location, such as for further analysis and processing, such as by a health professional.

System 10 (or system 10A) or device 10 may also include circuits for the data collection, data storage and/or data transmission. In certain preferred embodiments, real-time clock data (for example associated with the location where the pet animal is located) is also transmitted to and received by processor 60 in order to include in its processing the various cycles of a pet animal's physiology. To take one example of the various cycles of a pet animal's physiology, there may be natural cycles of core temperature through the various parts of the daily cycle that may be transmitted to the processor 60 for inclusion in the processing. As another example, a waking state of the pet animal may be determined and transmitted to the processor 60. Accordingly, processor 60 may receive and process, depending upon the exact embodiment, all, or at least two, or at least one, of (i) the animal kind and/or size, (ii) the waking state of the animal and (iii) real-time clock data.

As shown in FIG. 2 and FIG. 3A, ambient temperature sensor 40 and skin temperature sensor 30 may be located at an external surface of the housing 90 or electronic compartment 90, in order to have free access to the ambient environment and to the pet animal's body surface respectively. Accordingly, the ambient temperature sensor 40 may have an exposed surface for sensing the ambient temperature and the skin temperature sensor 30 may have a working surface configured to face the neck or other body part of the pet. It should be noted that the term "skin temperature sensor" does not necessarily imply that there is no fur interposed between the skin of the pet animal and the skin temperature sensor and accordingly the teen "surface temperature sensor" may be used herein to refer more generally to a temperature sensor for the surface of the body of the pet animal, which may be the skin.

Electrical and mechanical characteristics of the skin temperature sensor 30 and of the ambient temperature sensor 40 may be configured to be identical or within a certain deviation, for example 10% (or another number between 5% and 20%). For example, the surface area of the heat collection surface of the ambient temperature sensor 40 and the surface area of the heat collection surface of the skin temperature sensor 30 may be configured to be identical or at least to be within a certain deviation of identical. For example in certain preferred embodiments the surface areas of the heat collection surfaces of sensors 30, 40 may be configured to be identical or plus or minus 10%, and in other preferred embodiments they may be identical or plus or minus 5% and in still other preferred embodiment identical or plus or minus a number between 5% to 20%. Maintenance of close or identical characteristics such as the above is one way of ensuring that the changes in skin temperature and changes in ambient temperature are reflected in new readings of the skin sensor 30 and ambient temperature sensor 40 at approximately the same time—that it takes approximately the same time for a given change in temperature to be reflected in a new reading from each sensor.

A further characteristic that may be maintained close or identical to ensure this, is to use similar or identical materials in the compositions of these two sensors 30, 40. Accordingly, the skin temperature sensor and the ambient temperature sensor may be made of the same material. Since when the temperature changes, the sensors of the same material and size will take the same amount of time to react, this may allow the system to compare simultaneous outputs from the ambient temperature sensor and the skin temperature sensor without having to correct for differences in the time it takes for each sensor to react to the new temperature. Accordingly, the surface area of the exposed surface of the ambient temperature sensor 40 may be configured to correspond in size with the surface area of the working surface of the skin temperature sensor 30. Other characteristics of sensors 30, 40 that may be maintained identical or within a certain deviation (such as 10%, or another percent between 5 and 20) are its electrical parameters such as nominal resistance value and resistance temperature coefficient. In certain preferred embodiments, all of the above characteristics of sensors 30, 40 are maintained identical or within a certain deviation while in certain other preferred embodiments at least one or at least two of the above characteristics of sensors 30, 40 are maintained identical or within a certain deviation. An example of three characteristics being maintained equal or within a certain deviation is: the same material is used in each sensor 30, 40, the resistance value and resistance temperature coefficient of each sensor is within 10% and the respective surface area of each sensor is within 10% (i.e. the surface area of the working surface of sensor 30 and the surface area of the exposed surface of sensor 40).

Figure 4:
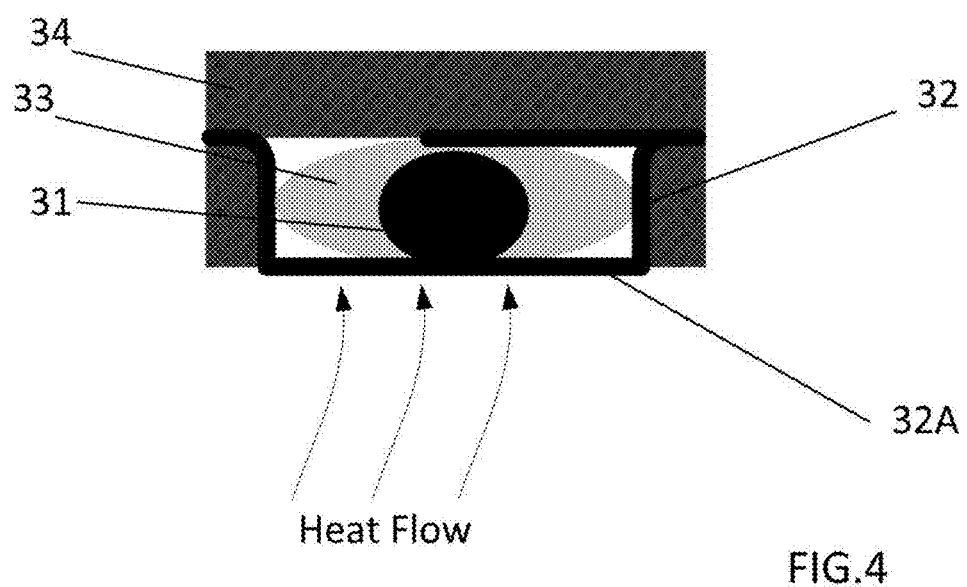
FIG. 4 is a sectional view of a thermistor assembly, in accordance with one embodiment of the present invention.

FIG. 4 shows a temperature sensor assembly housing 34 in one preferred embodiment. The temperature sensor assembly housing 34 may be thermo-isolated other than at the heat collection surface 32a of metal cap 32. A temperature sensor 31, for example in the particular embodiment shown in FIG. 4 may sit in metal cap 32, for example on a bottom surface 32a of metal cap 32, which may be a heat collection surface 32a of metal cap 32. Temperature sensor 31 may be surrounded by a substance such as a thereto-conductive glue and/or grease 33 that is designed to ensure that the heat flows to all parts of the temperature sensor 31 equally. In a preferred embodiment, the heat collection surface 32a of metal cap 32 may face the neck or other part of the body of the animal in the case of the skin surface temperature sensor 30. If the heat collection surface 32a of metal cap 32 is part of the ambient temperature sensor, however, the heat collection surface 32a may face outward away from the animal's body. Although cap 32 has been described as metal in a preferred embodiment, this is not a limitation, and cap 32 may, for example, be produced from any material having thermo conductivity equivalent to a metal.

As shown in FIG. 2, FIG. 2A, FIG. 3A, FIG. 3B and FIG. 3C, system 10 may also comprise a mounting device 70 for mounting at least the sensing assembly 20, and in some preferred embodiments also the processor 60, on the pet animal. The mounting device 70 may be a belt or collar or jacket or harness having an outer surface and an inner surface, the inner surface configured to conform to a part of the pet animal's body that the device 10 (or that system 10 other than the processor) is targeted to. The mounting device 70 may be configured for cushioning repetitive instances of friction against the collar 70 from movement of the body of the pet animal. Although the remainder of this application may refer primarily to the "neck" of the pet animal, since that is the preferred part of the body of the animal for situating the collar 70 in a preferred embodiment, it should be understood that in certain embodiments other portions of the animal may also hold the device 10 (or for example system 10 other than a processor 60 that is remote). It is noted that FIGS. 2 and 2A are schematic illustrations and are not intended to suggest that there is necessarily a space between mounting element 70 and the pet animal's body (although in some cases there may in fact be fur between the animal body and the mounting element 70).

As seen from the flow chart of FIG. 5 depicting one preferred embodiment having steps 322 through 906 (some of which run in parallel), the data from a 3D accelerometer is passed through a high pass filter (in step 326) to eliminate constant Earth gravity effect to get dynamic acceleration caused by motion. The dynamic data is used to calculate vector length, using usual formula $|G|=\sqrt{G_x^2+G_y^2+G_z^2}$. See, for example, Qasem L, Cardew A, Wilson A, Griffiths I, Halsey LG, et al. (2012) Tri-Axial Dynamic Acceleration as a Proxy for Animal Energy Expenditure; Should We Be Summing Values or Calculating the Vector? PLoS ONE 7(2): e31187. doi:10.1371/journal.pone.0031187 for the details of this method of activity estimation.

In a preferred embodiment, this value is calculated for every data sample (where number of samples depends on the sampling rate and measurement interval). These values may then be averaged by the entire interval of observation (typically, 30 sec-2 minutes) to obtain a single value—activity A. This value may be converted into 0 . . . 100 range for the convenience. The conversion can be performed using the division by the value of normal Earth gravity of 1 g followed by the logarithmation of the result.

Temperature data from the temperature sensors (at least, one sensor for the skin surface temperature, and one sensor for the ambient temperature) are processed as it is required by sensor design to obtain temperature in common units (e.g. degrees of Celsius, or Fahrenheit). The number of temperature samples depends on the sensor sampling rate and measurement interval.

In a preferred embodiment, the temperature values may be averaged over the measurement interval to get two values: average skin surface temperature and average ambient temperature. These temperatures are used to calculate the heat flow estimation in the form of the temperature difference: $J=T_S-T_A$, where J is the heat flow, $T_A$ is the ambient temperature, and $T_S$ is the skin surface temperature.

The values A and J may be buffered (collected from several measurement intervals) and synchronized in time (re-sampled and/or interpolated to the common time scale if required).

Both A and J along with some configurable model parameters (e.g. correlation coefficients, weights, and thresholds, etc.) that may depend on the animal's individuality (for example breed and size) are passed to the "Model Correlation" stage.

The system may include optional sensors (i.e. sensors for heart rate and breath rate measurements). One of these sensors may be a real-time clock for adjustment to the physiological cycles of the animal (e.g. circadian and seasonal changes in metabolism).

On the model correlation stage the data is tested for the model fitness. If the data fits the model, the core temperature is assumed to be in the appropriate range. Otherwise, an appropriate alert may be generated and may be displayed.

Note that the model, which embodies the relationship between the variables, may also be graphically represented, in which case it may also be referred to as a "graph". As shown in FIG. 6, the model demonstrates dependency between ambient ($T_A$) and body surface ($T_S$) temperatures for healthy animals. The model in its typical implementation utilizes linear dependency between ambient and body surface temperatures. The model can include calculation of a confidence interval for the fitness which allows configurable alert generation.

As seen from FIG. 6, the ambient temperature is conveniently divided to four intervals, where some intervals may be omitted if less informative results are acceptable. Comprehensive discussion of these intervals and temperatures along with underlaying concept of the Thermo Neutral Zone (TNZ) as well as discussion of their dependencies on the animals' properties can be found in the book by Kenneth Blaxter entitled "Energy Metabolism in Animals and Man" published by Cambridge University Press, NY, 1989 as well as in the references found in this book.

The intervals edges (on the ambient temperature axis) are:

$T_f$—freezing temperature. The animal is not capable to maintain proper temperature at this temperature and below.

$T_{lc}$—lower critical temperature. At this temperature and down to the $T_f$ the animal should increase its metabolism rate to keep core temperature at required value.

$T_{uc}$—upper critical temperature. At this temperature and above the animal should use additional means for the heat release (e.g., sweating, or panting).

$T_{min}$—the minimal tolerable temperature of the baseline. The temperature of a healthy animal's skin is always above or equal to the ambient temperature.

$T_{max}$—the maximal tolerable temperature of the baseline. The temperature of healthy animal's skin is always below or equal to the animal's core temperature.

The values of Tf, Tlc, Tuc and corresponding values of $T_S$ including $T_{min}$ and $T_{max}$, depend on the animal kind and size and are model parameters.

As seen from FIG. 6, the correlation between $T_S$ and $T_A$ is linear inside of each of the zones:

$T_S=a_1*T_A\ b_1$, inside the TNZ (Tlc<$T_A$<TUC),
$T_S=a_2*T_A+b_2$, in the zone below Tlc ($T_A$=<Tlc),
$T_S=a_3*T_A\ b_3$, in the zone above Tuc ($T_A$>=Tuc), where the correlation coefficients (a, b) may depend on the animal kind and size.

These values define the model baseline (shown as the bold line in FIG. 6) at minimal (resting) activity during non-sleeping period (i.e., daytime for the dogs).

Activity level data for the animal determines maximal (upper) model tolerance range (upper and lower margins). The higher activity, the higher heat transfer is required. Thus, at high activity levels the temperature of the body surface may be higher that defined by the baseline of the temperature regulation model. For example, at high activity level (e.g. active running) the upper margin can be at baseline+15 degrees Celsius, while at low activity (near resting) the upper margin can be baseline+2 degrees Celsius. The lower margin of the model is necessary to detect possible hypothermia and/or abnormal inactivity states like depression. Both margins depend on the properties of the animal and may depend on time of the day, or season. For example, during sleeping time the baseline may coincide with the lower margin.

The upper and lower margins appear in FIG. 6 as dashed lines parallel to (at least in two of the zones) the bold line and designated by arrows.

In a preferred embodiment of the method of the present invention the model tolerance range can be presented as linearly dependent on the activity level of the animal as:
upper margin=$c_1*A+d_1$,
lower margin=$c_2*A+d_2$, where correlation coefficients $c_i$ and $d_i$ depend on the activity units and properties of the animal, such as the animal kind and size.
The parameters of the model may also depend on time to utilize daily and seasonal cycles of the animal's physiology.

In accordance with a preferred embodiment of a system, method and/or apparatus of the present invention, the following algorithm may be utilized to monitor whether the pet animal is in a normal range for core temperature:
1. take the measured $T_A$, $T_S$, and activity A
2. use $T_A$ to find the working interval of the model (inside TNZ, below Tlc, etc)
3. take one or more appropriate correlation coefficients ($a_i$, $b_i$)
4. calculate baseline of the model: Tmodel=$a_i*T_A+b_i$
5. use activity A and coefficients ($c_j$, $d_j$) to calculate the tolerance range: lower margin=$c_1*A+d_1$, upper margin=$c_2*A$ $d_2$
6. if lower margin<=Tmodel<=upper margin then core temperature is in appropriate range. Otherwise, display an indication that the core temperature is abnormal.

For example, the temperatures and coefficients values for the medium size dog (e.g. golden retriever) with the device mounted on its neck as a collar, are:

$T_f$, $T_{lc}$, $T_{uc}$ are −10, +22, and +27 degrees Celsius respectively $T_{max}$=+39.2 degrees Celsius, and $T_{min}$=+25 degrees Celsius $a_1$=1, $b_1$=4, $a_2$=−1, $b_2$=48, and $a_3$=0.7, $b_3$=11.4

$c_1$=0.15, $d_1$=2, $c_2$=0, $d_2$=−3 ($d_2$=0 during the sleep time) for the normalized activity As shown in FIG. 2, FIG. 3A, FIG. 313 and FIG. 3C, signals received as outputs from skin temperature (surface temperature) sensor 30 and from ambient temperature sensor 40, as well as from accelerometer 50 either in analog or digital form may be collected by processor 60, which may implement data processing, for example in accordance with the flow chart depicted in FIG. 5.

The device, system and method of the present invention may be said to be measuring whether the animal's core temperature is assumed to be in a normal range for that animal and vice versa.

Figure 7:
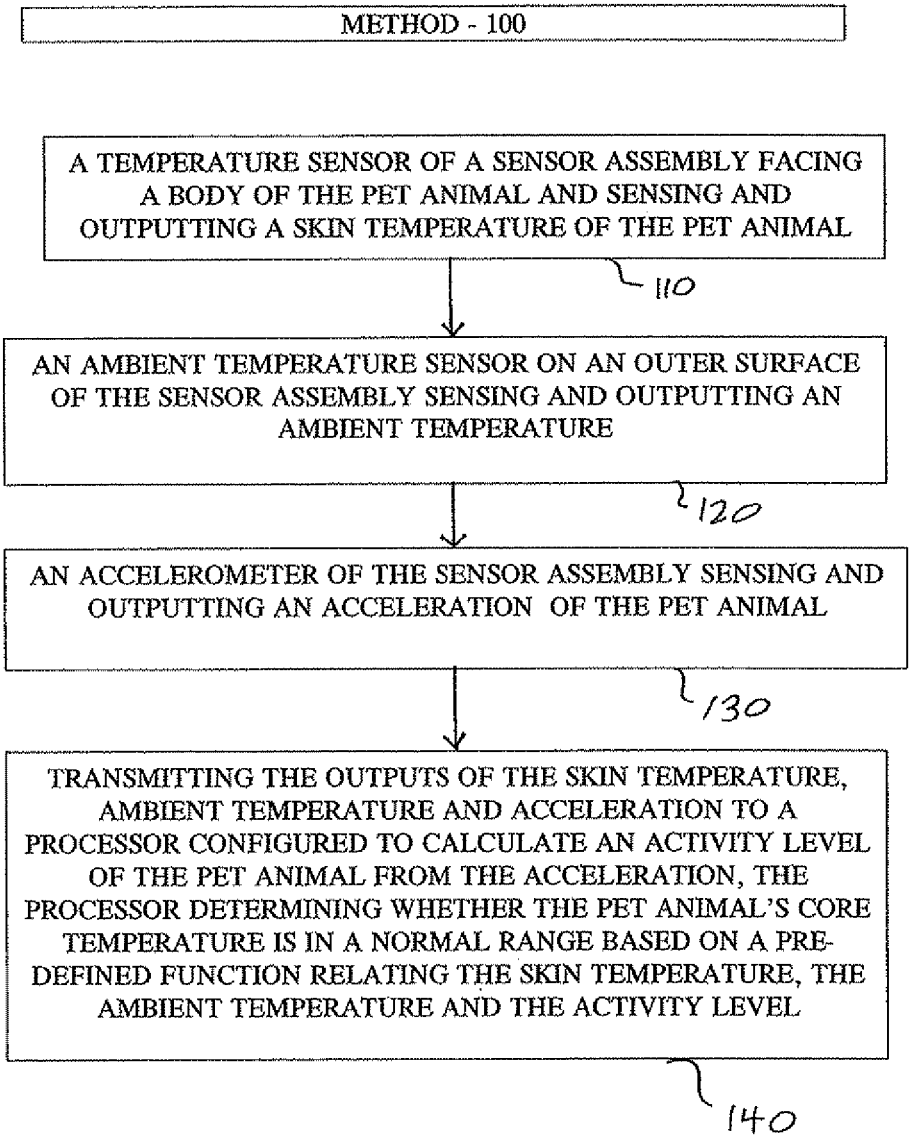
FIG. 7 is a flow chart showing a method, in accordance with one embodiment of the present invention.

As shown in FIG. 7, the present invention may also be described as a method 100 of estimating (or a method of monitoring) a core temperature of a pet animal. Method 100 may comprise a step 110 of a temperature sensor of a sensor assembly facing a body of the pet animal and sensing and outputting a skin temperature of the pet animal. This may be accomplished for example mounting a sensor assembly on the body of a pet animal such that a temperature sensor facing the body senses and outputs a skin temperature of the pet animal. Method 100 may also have a step 120 of an ambient temperature sensor on an outer surface of the sensor assembly sensing and outputting an ambient temperature. Step 130 may comprise an accelerometer of the sensor assembly sensing and outputting an acceleration of the pet animal. Method 100 may have a step 140 of transmitting the outputs of the skin temperature, ambient temperature and acceleration to a processor configured to calculate an activity level of the pet animal from the acceleration. Step 150 may comprise the processor determining whether the pet animal's core temperature is in a normal range based on a pre-defined function relating the skin temperature, the ambient temperature and the activity level.

Method 100 may have a further step of having the processor determine whether the core temperature is in the normal range by determining whether the skin temperature is within a confidence interval. For example, method 100 have a step of having the processor determine the confidence interval based on the outputted ambient temperature, the outputted skin temperature and the outputted acceleration. In a preferred embodiment, the step of method 100 may be having the processor determine the confidence interval based on a kind and/or a size of the pet animal and based on the ambient temperature output, the skin temperature output and the acceleration output. Method 100 may also have a step of positioning the sensor assembly (including the skin temperature sensor, the ambient temperature sensor and the accelerometer) non-invasively relative to the pet animal.

Method 100 may also include a step of configuring the processor to determine whether the pet animal's core temperature is in the normal range by relating the skin temperature $T_S$ to the ambient temperature $T_A$ within a tolerance range that is dependent on the activity level of the pet animal. A step of method 100 may also comprise configuring the processor to utilize an equation $T_S$=$a*T_A$+b that is operative within a certain range of $T_A$, wherein $T_S$ is a variable of the skin temperature, $T_A$ is a variable of the ambient temperature and a and b are coefficients that are set depending upon the range of $T_A$ as well as an animal size and kind. According to a step of method 100, the processor may be configured to utilize equations defining an upper margin of the skin temperature to be equal to $c_1*A+d_1$, and defining a lower margin of the skin temperature to be equal to $c_2*A+d_2$, wherein A is the activity level and wherein coefficients $c_i$ and $d_i$ are set depending upon activity units and depending upon animal kind and/or size.

Method 100 may include a step of configuring the processor to take into consideration a zone of the ambient temperature.

Any other suitable aspects of the algorithm and/or model discussed relating to the system and device of the present invention may be incorporated into a method of the present invention.

Figure 8:
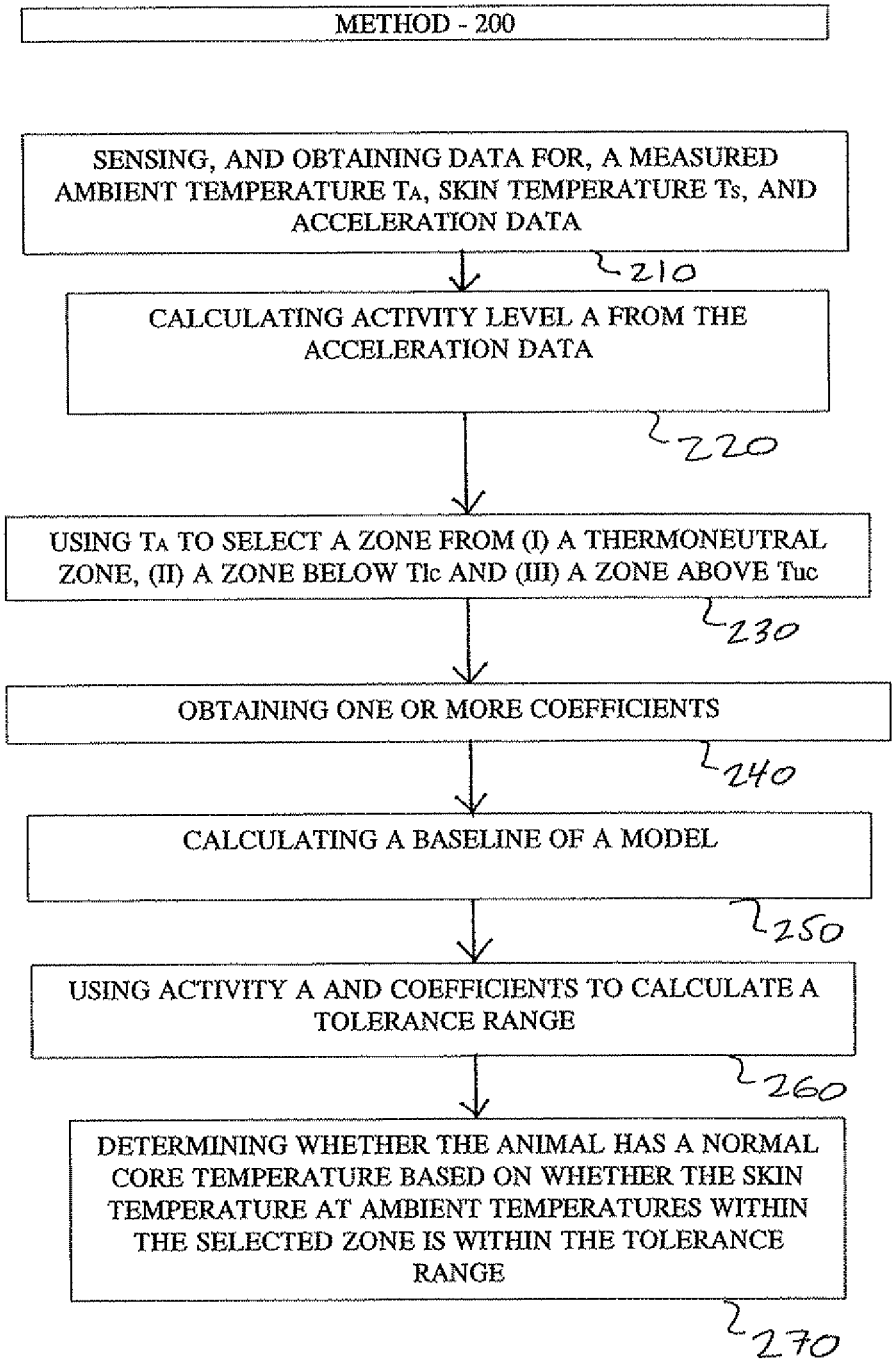
FIG. 8 is a flow chart showing a further method, in accordance with one embodiment of the present invention.

As shown in FIG. 8, the present invention may be described as a method 200 of determining if an animal's core temperature is within a normal range. Method 200 may comprise a step 210 of sensing and obtaining data for the measured ambient temperature $T_A$, skin temperature $T_S$, and acceleration data. A step 220 may invoice calculating activity A from the acceleration data, for using a separate algorithm. Method 200 may also comprise a step 220 of using $T_A$ to select a zone (i.e. the working interval of the model) from among (i) a thermoneutral zone TNZ, (ii) a zone below Tlc and (iii) a zone above Tuc. Step 230 may comprise obtaining the appropriate correlation coefficients ($a_i$, $b_i$). A further step 240 of method 200 may be calculating the baseline of the model: Tmodel=$a_i*T_A+b_i$. Step 250 may comprise using activity A and coefficients (for example coefficients ($c_j$, $d_j$)) to calculate the tolerance range: lower margin=$c_1*A+d_1$, upper margin=$c_2*A+d_2$. Step 260 of method 200 may be determining whether the animal has a normal core temperature based on whether the skin temperature at ambient temperatures within the selected zone is within the tolerance range. For example, if lower margin<=Tmodel<=upper margin the core temperature is determined to be in the appropriate range. Method 200 may also have a step of signaling abnormal core temperature if it the skin temperature at ambient temperatures within the selected zone is not within the tolerance range.

Method 100 or method 200 may include a step of configuring the ambient temperature sensor to be at least two centimeters (or some other appropriate distance) from the skin temperature sensor. Method 100 or the "further method" may also include a step of situating the processor at a location remote from the sensor assembly and transmitting signals comprising the outputs from the sensor assembly to the processor at the remote station.

The method may also include, in some embodiments, a step of transmitting the determination of the processor to the pet owner, a veterinarian, a remote computer server or the authorities when the core temperature measurement falls outside a normal range. In addition, the processor 60 may have access to its own data comparing the physiological data of the animal's core temperature to the average core temperature for pets of that species, that breed and that geographical location. The controller/processor may transmit an alert to the pet owner, to a veterinarian or to the authorities.

Particular features described in the context of one embodiment may be able to be incorporated into other embodiments for which that feature was not specifically mentioned.

Applicant has conducted experiments in which a particular pet animal of a particular size and species was monitored for skin surface temperature while simultaneously monitoring the ambient temperature and the activity level of the pet animal. These experiments have lead applicant to unexpectedly discover that the aforementioned equations can be used to determine the health of the animal and that particular coefficients for the equations depend on the kind and size of the pet animal.

This patent application hereby incorporates by reference in its entirety the Applicant's previously filed U.S. Patent Application having Publication No. 20130014706 published Jan. 17, 2013 having the Title "Pet Animal Collar for Health and Vital Signs Monitoring, Alert & Diagnosis" and having a filing date of Feb. 21, 2012. The present invention may incorporate any suitable feature described in that patent application.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A system for monitoring a health of a warm-blooded pet animal including non-invasively monitoring and providing early detection of whether a core temperature of the warm-blooded pet animal is within a normal range for the pet animal, wherein the pet animal is a dog or cat, the system comprising:
   a non-invasive collar, including an elastic band, for positioning on a neck of the pet animal, the collar having an outer surface and an inner surface, the collar configured to output signals for ambient temperature, skin temperature, at least one of heart rate and respiration and at least one of posture and movement of the pet animal, while being positioned on a single integrally connected body part of the pet animal,
   the collar including a sensing assembly having sensors positioned at different points along the collar including (i) a skin temperature sensor positioned such that a sensing surface of the skin temperature sensor faces a body of the pet animal, the skin temperature sensor configured to produce a skin temperature output, (ii) an ambient temperature sensor positioned on the outer surface and configured to produce an ambient temperature output, (iii) an accelerometer for sensing an acceleration level of the pet animal and producing an acceleration level output including posture and movement of the pet animal and (iv) an acoustic sensor configured to measure the at least one of heart rate and respiration and output at least one signal representing vital sign data for the at least one of heart rate and respiration, the acoustic sensor having multiple elastic projections of a substantially same length that face the neck and that are configured in shape to penetrate a fur of the dog or cat and to absorb noise from friction due to movement of a head of the dog or cat, the absorption of the noise increasing a signal to noise ratio of the at least one signal conducted to the acoustic sensor, the length running radially from the collar to the neck; and
   one or more processors configured to receive the skin temperature output, $T_S$, the ambient temperature output $T_A$, and the acceleration level output and to determine an activity level, A, of the pet animal from the acceleration level output,
   the one or more processors also configured to
   (i) use $T_A$ to select a zone from one of three zones including (i) a thermoneutral zone, (ii) a zone below lower critical temperature (Tlc) and (iii) a zone above upper critical temperature (Tuc);
   (ii) use a pre-defined function $T_{MODEL}=a*T_A+b$ to calculate from $T_A$ a baseline model skin temperature, wherein $T_A$ is a variable of the ambient temperature output and a and b are coefficients that are set depending upon an animal size and kind and the selected zone of $T_A$, wherein, in each of the three zones, the baseline model skin temperature varies across varying values of $T_A$;
   (iii) use $c_1*A+d_1$ to calculate from activity A and coefficients ($c_i$, $d_i$) an adjustment of the baseline model skin temperature yielding a lower margin of a tolerance range and to use $c_2*A+d_2$ to calculate from activity A and coefficients ($c_i$ and $d_i$) an adjustment of the baseline model skin temperature yielding an upper margin of the tolerance range, wherein coefficients $c_i$ and $d_i$ are set depending upon activity units and animal kind or size and
   (iv) determine if Ts is within the tolerance range, and to determine if the core temperature is within the normal range under a rule that if, and only if, Ts is within the tolerance range the core temperature of the pet animal is within the normal range
   the system is configured to operate in ambient temperature environments spanning the three zones.

2. The system of claim 1, wherein the accelerometer and one or more processors are configured to also detect an indication of at least one of the following postures of the dog: lying on back, trotting, running, urinating (male/female), defecating, scratching hind leg.

3. The system of claim 1, wherein the one or more processors is also configured to receive, as part of the acceleration data, (i) a waking state of the pet animal, (ii) real-time clock data, and (iii) animal kind and/or size.

4. The system of claim 1, wherein the accelerometer and one or more processors are configured to also detect an indication of at least two of the following postures of the dog: lying on back, trotting, running, urinating (male/female), defecating and scratching hind leg.

5. The system of claim 1, wherein the following characteristics of the surface temperature sensor and the ambient temperature sensor are within ten percent of one another: (i) nominal resistance value, (ii) resistance temperature coefficient and (iii) a surface area of a heat collection surface.

6. The system of claim 1, wherein the skin temperature sensor and the ambient temperature sensor are made of the same material.

7. The system of claim 1, wherein the multiple elastic projections are elongated.

8. The system of claim 1, wherein the pet animal has a body including a neck and a non-neck portion and wherein the system is configured to monitor the health and provide the early detection using the collar and the one or more processors without having to cover the non-neck portion of the pet animal.

9. The system of claim 1, wherein the accelerometer and one or more processors are configured to also detect an indication of at least three of the following postures of the dog: lying on back, trotting, running, urinating (male/female), defecating and scratching hind leg.

10. A method of monitoring a health of a pet animal including non-invasively monitoring and providing early detection of whether a core temperature of the pet animal is within a normal range for the pet animal, the pet animal being a dog or cat, the method comprising:

providing a non-invasive collar having an outer surface and an inner surface, the inner surface configured with multiple elastic projections projecting toward the neck of the pet animal, the collar including an elastic band, providing the collar with a temperature sensor of a sensor assembly facing a body of the pet animal and sensing and outputting a skin temperature of the pet animal;

providing the collar with an ambient temperature sensor on an outer surface of the sensor assembly sensing and outputting an ambient temperature;

providing the collar with an accelerometer of the sensor assembly sensing and outputting an acceleration of the pet animal including by detecting movement and posture of the pet animal;

providing the collar with an acoustic sensor sensing and outputting at least one of a heart rate and a respiration rate of the pet animal, the acoustic sensor having the multiple elastic projections being of a substantially same length and configured in shape to penetrate a fur of the dog or cat and to absorb noise from friction due to movement of a head of the dog or cat, the absorption of the noise increasing a signal to noise ratio of a signal conducted to the acoustic sensor, the length running radially from the collar to the neck;

transmitting the outputs of the skin temperature, ambient temperature and acceleration to one or more processors configured to calculate an activity level, A, of the pet animal from the acceleration output, the processor determining whether the pet animal's core temperature is in a normal range based on a pre-defined function relating the skin temperature, the ambient temperature and the activity level;

configuring the one or more processors either on or remote from the collar to (i) use $T_A$ to select a zone from one of three zones including (i) a thermoneutral zone, (ii) a zone below lower critical temperature (Tlc) and (iii) a zone above upper critical temperature (Tuc);

(ii) use the pre-defined function $T_{MODEL} = a*T_A + b$ to calculate from $T_A$ a baseline model skin temperature, wherein $T_A$ is a variable of the ambient temperature and a and b are coefficients that are set depending upon an animal size and kind and on the selected zone of $T_A$, wherein, in each of the three zones, the baseline model skin temperature varies across varying values of $T_A$, (iii) use $c_1*A+d_1$ to calculate from activity A and coefficients ($c_i$, $d_i$) an adjustment of the baseline model skin temperature yielding a lower margin of a tolerance range and to use $c_2*A+d_2$ to calculate from activity A and coefficients ($c_i$ and $d_i$) an adjustment of the baseline model skin temperature yielding an upper margin of the tolerance range, wherein coefficients $c_i$ and $d_i$ are set depending upon activity units and animal kind or size and (iv) determine if Ts is within the tolerance range, and to determine if the core temperature is within the normal range under a rule that if, and only if, Ts is within the tolerance range the core temperature of the pet animal is within the normal range, the one or more processors determining a health of the pet animal from the outputs of the sensor assembly and the output of the acoustic sensor.

11. The method of claim 10, further comprising positioning the sensor assembly and processor of the pet animal non-invasively in relation to the pet animal.

12. The method of claim 10, further comprising configuring the ambient temperature sensor to be at least two centimeters from the skin temperature sensor.

13. The method of claim 10, further comprising situating the one or more processors at a location remote from the sensor assembly and transmitting signals comprising the outputs from the sensor assembly to the one or more processors at the remote station.

14. The method of claim 10, wherein the accelerometer and one or more processors are configured to also detect an indication of at least one of the following postures of the dog: lying on back, trotting, running, urinating (male/female), defecating and scratching hind leg.

15. A method of monitoring a health of a pet animal including non-invasively monitoring and providing early detection of whether a pet animal's core temperature is within a normal range, the pet animal being a dog or cat, comprising:

using sensors in a non-invasive collar, the collar including an elastic band, positioned on a neck of the pet animal, sensing, and obtaining data for, a measured ambient temperature $T_A$, skin temperature $T_S$, and acceleration data, the sensors including (i) a skin temperature sensor positioned such that a sensing surface of the skin temperature sensor faces a body of the pet animal, the skin temperature sensor configured to produce a skin temperature output Ts, (ii) an ambient temperature sensor configured to produce an ambient temperature output, and (iii) an accelerometer for sensing an acceleration level of the pet animal and producing an acceleration level output including posture and movement of the pet animal;

using one or more processors to:

(i) calculate activity level, A, from the acceleration data;

(ii) use $T_A$ to select a zone from one of three zones including (i) a thermoneutral zone, (ii) a zone below lower critical temperature (Tlc) and (iii) a zone above upper critical temperature (Tuc);

(iii) obtain one or more coefficients that are set depending upon an animal size and kind;

(iv) use a pre-defined function $T_{MODEL} = a*T_A + b$ to calculate from $T_A$ a baseline model skin temperature, wherein $T_A$ is a variable of the ambient temperature output and a and b are coefficients that are set depending upon an animal size and kind and the selected zone of $T_A$, wherein, in each of the three zones, the baseline model skin temperature varies across varying values of $T_A$;

(v) use $c_1*A+d_1$ to calculate from activity A and coefficients ($c_i$, $d_i$) an adjustment of the baseline model skin temperature yielding a lower margin of a tolerance range and to use $c_2*A+d_2$ to calculate from activity A and coefficients ($c_i$ and $d_i$) an adjustment of the baseline model skin temperature yielding an upper margin of the tolerance range, wherein coefficients $c_i$ and $d_i$ are set depending upon activity units and animal kind or size and (vi) determine if Ts is within the tolerance range, and to determine if the core temperature is within the normal range under a rule that if, and only if, Ts is within the tolerance range the core temperature of the pet animal is within the normal range, the non-invasive collar including an acoustic sensor configured to measure at least one of heart rate and respiration rate and output at least one signal representing vital sign data for at least one of heart rate and respiration the acoustic sensor having multiple projections that face the neck and that are configured in shape to penetrate a fur of the dog or cat.

16. The method of claim 15, further comprising signaling abnormal core temperature if the skin temperature at ambient temperatures within the zone is not within the tolerance range.

17. The method of claim 15, wherein the projections of the acoustic sensor are elastic and of a substantially same length.

* * * * *